US00PP35349P2

(12) United States Plant Patent
Clark

(10) Patent No.: US PP35,349 P2
(45) Date of Patent: Aug. 22, 2023

(54) ***COLEUS* PLANT NAMED 'UF20-140-2'**

(50) Latin Name: *Coleus scutellarioides*
Varietal Denomination: UF20-140-2

(71) Applicant: Florida Foundation Seed Producers, Inc., Marianna, FL (US)

(72) Inventor: David G. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 17/803,907

(22) Filed: Jan. 13, 2023

(51) Int. Cl.
*A01H 5/12* (2018.01)
*A01H 6/50* (2018.01)

(52) U.S. Cl.
USPC ..... Plt./469

(58) Field of Classification Search
USPC ..... Plt./469
See application file for complete search history.

*Primary Examiner* — Susan McCormick Ewoldt
(74) *Attorney, Agent, or Firm* — Koenig IP Works, PLLC; Katherine Koenig

(57) ABSTRACT

A new and distinct cultivar of *Coleus* (*Coleus scutellarioides*) plant named 'UF20-140-2', selected for its combination of novel foliage shape and multi-colored patterning. It has multi-colored yellowish green foliage with dark red margins and accents, purplish red mid-veins, and pale greenish yellow bases. The foliage color shows stability in both sun and shade. The unique shape of the foliage is extremely uniform across the plant throughout development. It grows quickly under greenhouse production conditions and establishes well in the summer landscape. 'UF20-140-2' has an upright and spreading growth habit, but it is highly branched and uniform, growing wider than it does tall.

5 Drawing Sheets

Genus and species: *Coleus scutellarioides.*
Cultivar denomination: 'UF20-140-2'.

CROSS-REFERENCE TO RELATED APPLCIATIONS

N/A.

ACKNOWLEDGEMENT OF FEDERAL RESEARCH SUPPORT

N/A.

BACKGROUND OF THE NEW CULTIVAR

The invention relates to a new and distinct cultivar of *Coleus* plant named 'UF20-140-2'. The new cultivar 'UF20-140-2' originated from an open pollination conducted in May-November 2019 in Citra, Fla. between the female *Coleus* plant 'UF18-34-7' (unpatented) and an unknown male *Coleus* plant. A single seedling was chosen in May 2020 for further asexual propagation in Gainesville, Fla.

The new cultivar 'UF20-140-2' has been reproduced asexually for over 18 months through vegetative meristem tip cuttings and has been found to retain its distinctive characteristics through successive asexual propagations. 'UF20-140-2' was first propagated asexually by vegetative meristem tip cuttings in May 2020 in Gainesville, Fla., and has remained true-to-type since that time.

Plant Breeder's Rights for the new cultivar 'UF20-140-2' have not been applied for, and 'UF20-140-2' has not been made publicly available more than one year prior to the filing date of this application.

When compared to the female parent 'UF18-34-7', the new cultivar 'UF20-140-2' has small thin irregular shaped leaves that are twice as long as they are wide. Leaves of 'UF20-140-2' are multi-colored with yellowish green as the predominant color, with dark red margins and accents, purplish red mid-veins, and pale greenish yellow bases. In contrast, 'UF18-34-7' has larger leaves that are equally as long as they are wide, and lance-shaped with pointed apices. 'UF18-34-7' has leaves that are dark maroon with dark green margins, and only small traces of pink color on older leaves. 'UF20-140-2' has a vigorous upright and spreading growth habit, whereas 'UF18-34-7' is equally vigorous but has a distinctly mounding growth habit with more lateral branching.

The new cultivar 'UF20-140-2' was selected because it has a combination of novel and desirable traits. It has multi-colored yellowish green and dark red foliage, highlighted with purplish red and pale greenish yellow areas. The foliage color shows stability in both sun and shade. The unique shape of the foliage is extremely uniform across the plant throughout development. It has excellent lateral branching, thus providing ample vegetative propagules for producers. It has a vigorous upright and spreading habit, growing more horizontal than vertical, which allows it to fill space with vibrant color very quickly in summer gardens.

SUMMARY OF THE INVENTION

The new cultivar 'UF20-140-2' has not been observed under all possible environmental conditions. The phenotype of the new cultivar may vary with variations in environment and cultural practices such as temperature, light intensity, fertilization, irrigation, and application of plant growth regulators without any change in genotype.

The following are the most outstanding and distinguishing characteristics of 'UF20-140-2' when grown under normal horticultural practices in Gainesville, Fla.: 'UF20-140-

2' has the combination of vigorous, upright and spreading growth habit, excellent heat tolerance, and consistent multi-colored leaves that are significantly different than other *Coleus* plants; it has superior stability in foliage color in both sun and shade conditions, maintaining stable color in all conditions; 'UF20-140-2' is a vigorous cultivar with excellent lateral branching, making it suitable for propagators and producers; and 'UF20-140-2' has been observed to have long-season performance in landscape trials in Gainesville, Fla.

DESCRIPTION OF THE FIGURES

This new *Coleus* cultivar 'UF20-140-2' is illustrated by the accompanying photographs, which show the plant's form and foliage. The colors shown are as true as can be reasonably obtained by conventional photographic procedures.

FIG. 2 shows the growth habit, form, and foliage of the new *Coleus* cultivar;

FIG. 3 shows a close-up view of the foliage of the new *Coleus* cultivar;

FIG. 4 shows the adaxial side of an immature leaf (left) and a mature leaf (right) of the new *Coleus* cultivar, with corresponding R.H.S. color designations; and FIG. 5 shows the abaxial side of an immature leaf (left) and a mature leaf (right) of the new *Coleus* cultivar, with corresponding R.H.S. color designations.

DETAILED BOTANICAL DESCRIPTION OF THE CULTIVAR

Figure 1:
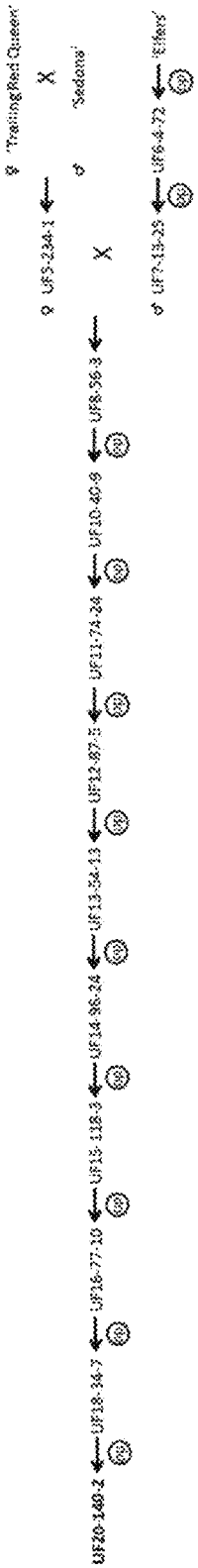
FIG. 1 shows the pedigree of the new *Coleus* cultivar 'UF20-140-2' as shown and described herein.
Figure 2:
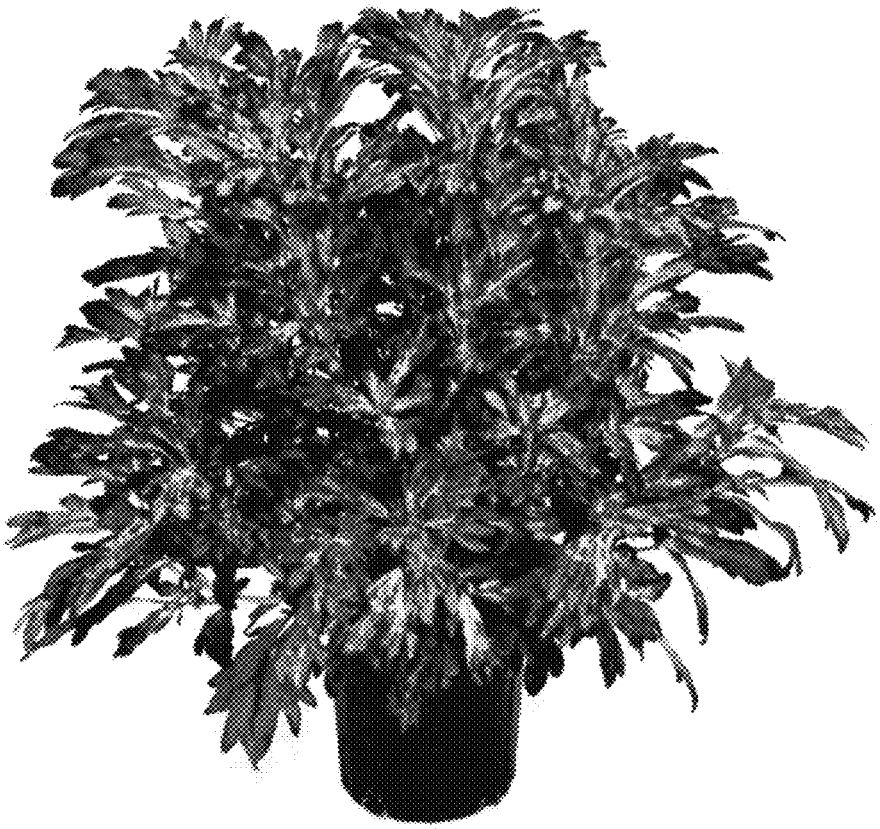
FIGS. 2-5 were taken from plants grown eight weeks from unrooted cuttings in July-September 2022 in a glass-covered greenhouse in Gainesville, Fla.
Figure 3:
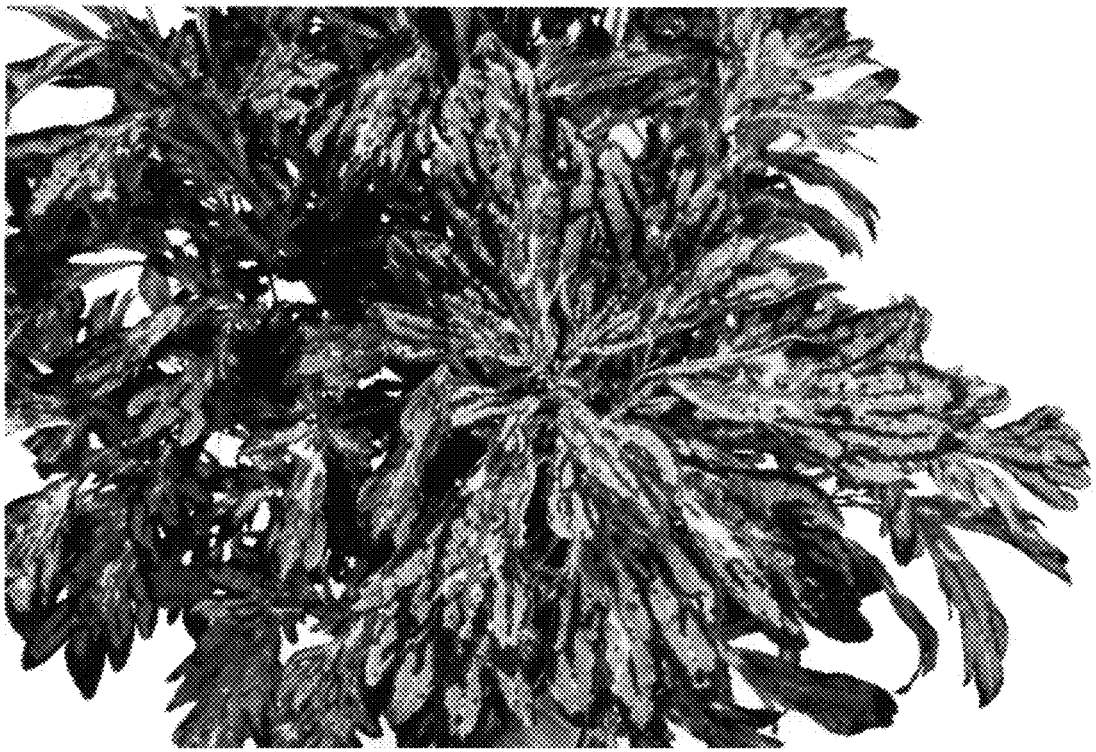
Figure 4:
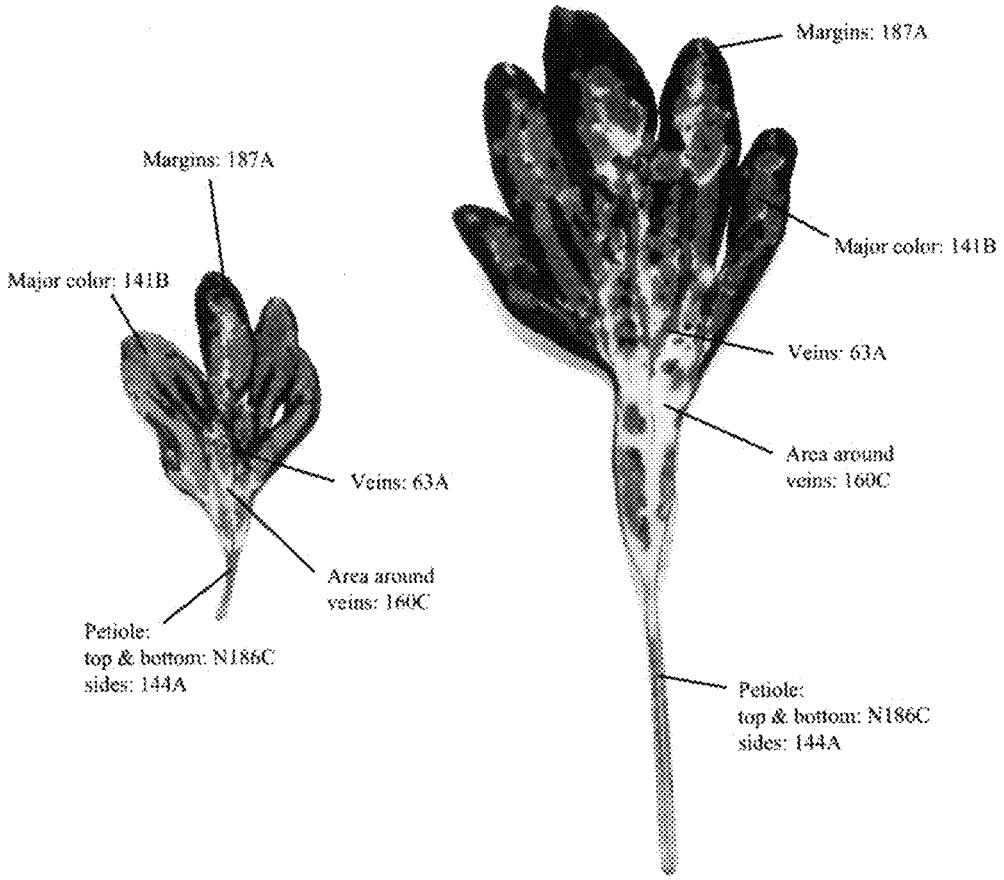
Figure 5:
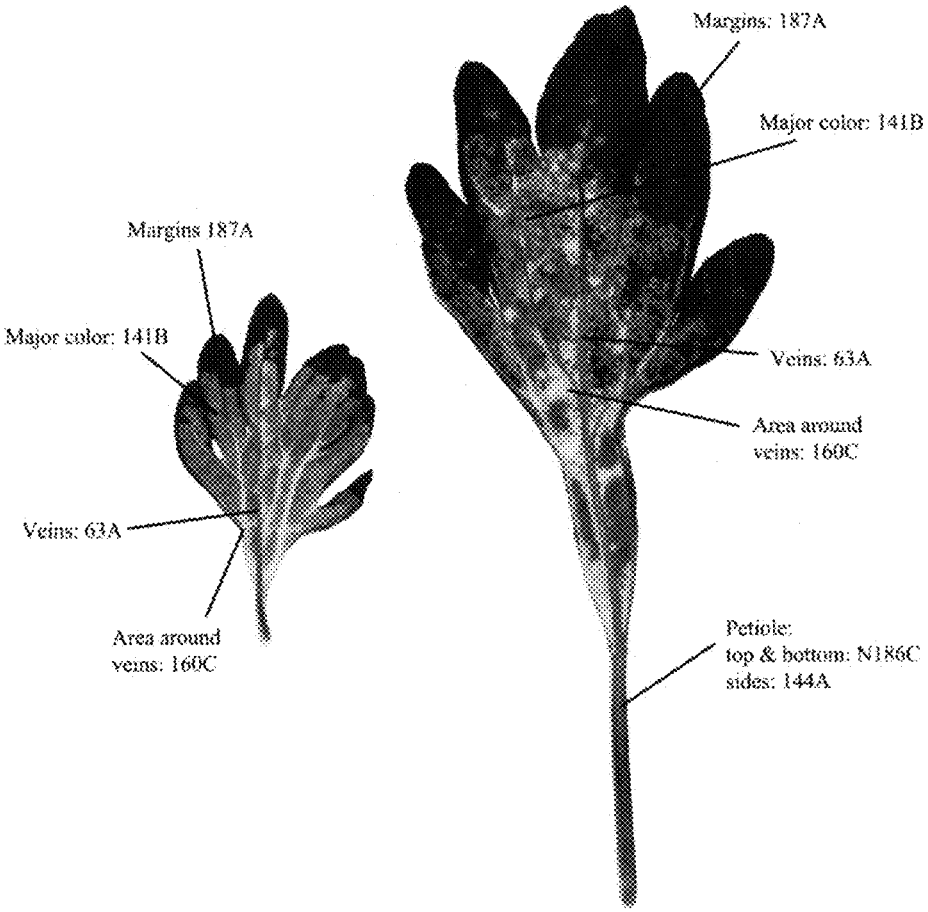

Foliage color was determined under full sun conditions in the middle of the day in a glass-covered greenhouse. Color references are to The R.H.S. Colour Chart of The Royal Horticultural Society of London (R.H.S.), 2007 5th Edition. *Coleus* leaves are rarely one solid color but encompass hues, shades and tints, and color patterns differ from one genotype to another due to varying levels of variegation. The following detailed description of 'UF20-140-2' was obtained using ten-week-old plants grown from unrooted cuttings in February-April 2022 in a glass-covered greenhouse in Gainesville, Fla. The plants were propagated in mist for ten days after cuttings were stuck, then grown in one-gallon pots for approximately eight and a half additional weeks.

Botanical Description

Botanical classification:
- *Family*.—Lamiaceae.
- *Botanical name*.—*Coleus scutellarioides*.
- *Common name*.—*Coleus*.
- *Cultivar*.—'UF20-140-2'.

Parentage:
- *Female or seed parent*.—'UF18-34-7'.
- *Male or pollen parent*.—Unknown.

Plant description:
- *Habit*.—Upright and spreading
- *Height* (*from top of soil*).—40-45 cm.
- *Width* (*horizontal plant diameter*).—65-70 cm.

Propagation:
- *Type cuttings*.—Vegetative meristem tip cuttings having at least 1 node.
- *Time to initiate roots*.—3-4 days.
- *Time to produce a rooted cutting*.—7-10 days.
- *Root habit*.—Fibrous.
- *Root description*.—Callus forms in 2-3 days, roots initiate in 3-4 days and become a highly branched cutting in 7-10 days.

Branches:
- *Quantity per plant*.—Approximately 11.
- *Branch color*.—RHS 143A (yellow green).
- *Texture*.—Smooth.
- *Pubescence*.—Not present.
- *Stem description*.—Square-shaped stem.
- *Branch diameter*.—0.8-0.9 cm at the base of a 13-cm-long branch.
- *Branch length*.—12-15 cm.
- *Internode length*.—3.5-4.0 cm measured at mid-branch.
- *Anthocyanin*.—Not present.

Foliage description:
- *Quantity of leaves per branch*.—22-24.
- *Arrangement*.—Opposite.
- *Fragrance*.—Not fragrant.
- *Shape*.—Ovate.
- *Length*.—9-10 cm.
- *Width*.—Approximately 5 cm.
- *Apex*.—Broadly Acute.
- *Base*.—Attenuate.
- *Margin*.—Lobed.
- *Leaf texture*.—Upper surface: Pulverulent. Lower surface: Smooth.
- *Venation color*.—Upper surface: RHS 63A (purplish red). Lower surface: RHS 63A (purplish red).
- *Venation pattern*.—Upper surface: Reticulate. Lower surface: Reticulate.
- *Color, immature leaf*.—Upper surface, major color: RHS 141B (yellowish green). Upper surface, margins, and accents: RHS 187A (dark red). Upper surface, around the veins: RHS 160C (pale greenish yellow). Lower surface, major color: RHS 141B (yellowish green). Lower surface, margins, and accents: RHS 187A (dark red). Lower surface, around the veins: RHS 160C (pale greenish yellow).
- *Color, mature leaf*.—Upper surface, major color: RHS 141B (greenish yellow). Upper surface, margins, and accents: RHS 187A (dark red). Upper surface, around the veins: RHS 160C (pale greenish yellow). Lower surface, major color: RHS 141B (greenish yellow). Lower surface, margins, and accents: RHS 187A (dark red). Lower surface, around the veins: RHS 160C (pale greenish yellow).
- *Petiole length*.—4.0-4.5 cm.
- *Petiole diameter*.—Approximately 0.2 cm.
- *Petiole color*.—RHS N186C (greyish red) and RHS 144A (yellow green) in a striated pattern.
- *Petiole texture*.—Smooth, no pubescence.

Flowers and seeds: Flowers and seeds have not been observed to date during formal trials in Gainesville, Fla.

Fruit/seed set: Fruit/seed not observed.

Disease and insect resistance: Disease and insect resistance is typical of the species, thus no claims are made of any superior disease or insect resistance with this cultivar. The most common insect pests observed on this plant in Gainesville, Fla. have been long-tailed or citrus mealybugs (*Pseudococcus* spp.), which occur on older stock plant material held in the greenhouse for over 3-4 months. *Impatiens* Necrotic Spot Virus (Bunyaviridae) has also been observed in plants confined in greenhouses with mixed crops (peppers) infected with Western flower thrips (*Frankliniella occidentalis*). The most common pathogen of this species in the U.S. is downy mildew (*Peronospora lamii*). This pathogen has been observed in stock materials grown closely together in cooler growing seasons.

Comparison with Known Cultivars

When the new cultivar 'UF20-140-2' is compared to the commercial cultivar 'UF20-138-1' (unpatented, commercial name "Mini Me Watermelon"), 'UF20-140-2' and 'UF20-138-1' have very similar leaf shape and growth habits; however, 'UF20-140-2' has mature leaves that are multicolored greenish yellow, pale greenish yellow and dark red on the upper surface, whereas 'UF20-138-1' has mature leaves that are predominantly colored dark red with yellow green margins and accents on the upper surface.

What is claimed is:

1. A new and distinct *Coleus scutellarioides* plant named 'UF20-140-2' as shown and described herein.

* * * * *